United States Patent [19]

Mayhew et al.

[11] Patent Number: 4,873,088

[45] Date of Patent: Oct. 10, 1989

[54] LIPOSOME DRUG DELIVERY METHOD AND COMPOSITION

[75] Inventors: Eric Mayhew, South Wales; M. Jane Ehrke, Lancaster; Kenneth Mace, Buffalo, all of N.Y.; Francis Szoka, San Francisco, Calif.; Fred C. Olson, Helena, Mont.

[73] Assignee: Liposome Technology, Inc., Menlo Park, Calif.

[21] Appl. No.: 72,828

[22] Filed: Jul. 13, 1987

Related U.S. Application Data

[63] Continuation-in-part of Ser. No. 529,890, Sep. 6, 1983, abandoned, and Ser. No. 915,863, Oct. 6, 1986, abandoned.

[51] Int. Cl.$^4$ .................. A61K 9/52; A61K 49/00; B01J 13/02
[52] U.S. Cl. .................. 424/450; 514/970; 514/974; 514/54
[58] Field of Search ............. 424/450; 514/970, 974, 514/54

[56] References Cited

U.S. PATENT DOCUMENTS

| | | |
|---|---|---|
| 4,331,648 | 5/1982 | Myers et al. ............... 424/10 |
| 4,372,949 | 2/1983 | Kodama et al. ............ 424/450 |
| 4,515,736 | 5/1985 | Deamer ...................... 424/88 |
| 4,544,545 | 10/1985 | Ryan et al. ................. 424/450 |
| 4,565,696 | 1/1986 | Health et al. .............. 424/450 |
| 4,619,794 | 10/1986 | Hauser ....................... 424/450 |
| 4,666,747 | 5/1987 | Quinn ......................... 514/65 |
| 4,687,762 | 8/1987 | Fukushima et al. ........ 514/78 |
| 4,746,516 | 5/1988 | Moro et al. ................ 514/34 |
| 4,756,910 | 7/1988 | Yagi et al. .................. 424/450 |

OTHER PUBLICATIONS

Rahman et al., Liposomal Protection of Adriamycin-Induced Cardiotoxicity in Mice, Canc. Res., 40:1532–1537, (1980).

Myers et al., Adriamycin Amelioration of Toxicity by α Tocopherol, Cancer Tx. Reports, 60:961–962, (1976).

Sonneveld, Effect of α Tocopherol on the Cardiotoxicity of Adriamycin in the Rat, Cancer Tx. Reports, 62:1033–1036, (1978).

Wang et al., Effect of Vit E Against Adriamycin-Induced Toxicity in Rabbits, Canc. Res., 49:1022–1027, (1980).

Forssen et al., *In Vitro* v *In Vivo* Studies with Adriamycin Liposomes, Biochem. Biophys. Res. Comm., 91-12-95–1301, (1979).

Forssen et al., Use of Anionic Liposomes for the Reduction of Chronic Doxorubicin-Induced Card., P.N.A.S., 78:1873–7, (1981).

Marlow et al., Reduction of the Inhibitory Effect on Adriamycin on Myocardial Contraction in vitro by Entrapment of Lipo., Proc. Am. Assoc. Can. 2132.

Olson et al., Charact. Tox. and Ther. Efficacy of Adriamycin on Capsulated in Lyposomes, Eur. J. Cancer, (in Press).

Hunt et al., α-Tochopherol Retards Antioxidation and ProCongs the Shelf Life of Liposomes, Int. J. Pharm. 8:101–110, (1981).

Primary Examiner—Ronald W. Griffin
Attorney, Agent, or Firm—Peter J. Dehlinger; Hana Dolezalova

[57] ABSTRACT

A method for enhancing the therapeutic effectiveness of adriamycin, in the treatment of cancer, is disclosed. Liposomes containing coentrapped adriamycin and a secondary compound effective to reduce the toxicity of adriamycin or enhance the induction by adriamycin of the tumoricidal activity of host lymphoid cells, such as lipopolysaccharide, are administered parenterally in a therapeutically effective dose. In another aspect, macrophages stimulated in vivo with liposomes containing entrapped liposomes are exposed to an immunostimulator, for enhanced tumoricidal activity. Also disclosed are liposome compositions containing coentrapped adriamycin and an immunostimulator.

17 Claims, 4 Drawing Sheets

LIPOSOME DRUG DELIVERY METHOD AND COMPOSITION

CROSS-REFERENCE TO RELATED APPLICATION

This application is a continuation-in-part of U.S. patent application Ser. No. 529, 890, filed Sept.6, 1983, now abandoned, and U.S. patent application Ser. No. 915,863, filed Oct. 6, 1986, now abandoned.

FIELD OF THE INVENTION

The present invention relates to improved tumor treatment methods and compositions.

REFERENCES

Aubel-Sadron, G., et al, Biochemie, 66: 333 (1984).

Cohen, S. A., Salazar, D. and Wicher, J. Adriamycin-induced Activation of NK Activity May Initially LAF Production. Cancer Immunol. Immunother., 15: 188–193 (1983).

Diplock, A. T., Lucy, J. A., Verrirder, M. and Zieliniewski, A. Alpha-tocopherol and the permeability to glucose and chromate of unsaturated liposomes. Febs Lett 82:341–344 (1977).

Doroshaw, J. H., et al, J Clin Invest 68:1053 (1981).

Ehrke, M. J., Maccubbin, D., Ryoyama, K., Cohen, S. A. and Mihich, E. Correlation Between Adriamycin-induced Augmentation of Interleukin-2 Production and of Cell-mediated Cytotoxicity in Mice. Cancer. Res. 46: 54–60 (1986).

Ehrke, M. J. and Mihich, E. Immunoregulation by Cancer Chemotherapeutic Agents. In: J. W. Hadden and A. Szentivanyi, A. (eds.), The Reticuloendothelial System: A Comprehensive Treatise, Vol. 8. The Pharmacology of the Reticuloendothelial System, pp. 309–347, New York, Plenum Press (1985).

Ehrke, M. J. and Mihich, E. Effects of Anticancer Agents on Immune Responses. Trends in the Pharm. Sci. 6: 412–417, 1985.

Ehrke, M. H. and Mihich, E. Adriamycin and Other Anthracyclines. In: M. S. Mitchell and J. L. Fahey (eds.) Clinics in Immunology and Allergy, 4: p. 259–273, Philadelphia, W. B. Saunders Co. (1984).

Ehrke, M. J., Cohen, S. A. and Mihich, E., Selective Effects of Adriamycin on Murine Host Defense Systems. Immunol. Rev. 65: 594–616 (1982).

Fidler, I. J., and Poste, G. Macrophage-mediated Destruction of Malignant Tumor Cells and New Strategies for the Therapy of Metastatic Disease. Springer Seminar in Immunopathology., 5: 161–174 (1983).

Fogler, W. and Fidler, I. J. Nonselective destruction of Murine Neoplastic Cells by Syngenic Tumoricidal Macrophages. Cancer Res. 45: 14–18 (1985).

Forssen, E. A. and Tokes, Z. A. Use of anionic liposomes for the reduction of chronic doxorubicin induced cardiotoxicity. Proc Nat Acad Sci USA 78: 1873–1877 (1981).

Forssen, E. A. and Tokes, Z. A. In vitro and in vivo studies with adriamycin liposomes. Biochem Biophys Res Comm 91:1295–1301 (1979).

Fukazawa, K., Ikeno, H., Takumura, A., and Tsukatini, H. Effect of alpha-tocopherol incorporation on glucose permeability and phase transition of lecithin liposomes. Chem Phys Lip 23:13–22 (1979).

Giavazzi, R., Bucana, C. D. and Hart, I. R. Correlation of Tumor Growth Inhibitory Activity of Macrophages Exposed to Adriamycin and Ariamycin Sensitivity of the target Tumor Cells. J. Nat. Cancer Inst. 73: 447–455 (1984).

Goormaghtigh, E., et al, Biochem Biophys Acta. 779: 271 (1984).

Haskill, J. S. Adriamycin-activated Macrophages as Tumor GrowthInhibitors. Cancer Res. 41: 3852–3856, (1981).

Hisano, G. and Fidler, I. J. Systemic Activation of Macrophages by Liposomes-entrapped Maramyl Tripeptide in mice pretreated with the Chemotherapeutic Agent Adriamycin. Cancer Immunol. and Immunother. 14: 61–66 (1982).

Hunt, C. A. and Tsang S. Alpha-tocopherol retards auto-oxidation and prolongs the shelf life of liposomes. Int J Pharmaceutics 8:101–110 (1981).

Juhl, H., et al, Biochem Biophys Res Commun 106(1):210 (1982).

Konigs, A. W. T., Darren, J., and Trieling, W. B. Protection of liposomal lipids against radiation induced oxidative damage. Int J Radiat Biol 35:343–350 (1979).

Mantovani, A., Polentarutti, N., Luini, W., Peri, G. and Spreafico, F. Role of Host Mechanism in the Antitumor Activity of Adriamycin and Daunomycin in Mice. J. Nat Cancer Inst. 63: 61 (1979).

Mantovani, A. In Vitro and In Vivo Cytotoxicity of Adriamycin and Daunorubicin for Murine Macrophages. Cancer Res. 36: 815–820 (1977).

Maslow, D. E., Mayhew, E., Olson F., and Rustum, Y. Reduction of the inhibitory effect of Adriamycin on myocardial contraction in vitro by entrapment in liposomes. Proc Am Assoc Cancer Res 21:281 (198).

Mayhe, E., Lazo, R. and Vail, W. J. Preparation of Liposomes Entrapping Cancer Chemotherapeutic Agents for Experimental In Vivo and In Vitro Studies. In: Gregoriadis, G. (ed.), *Liposome Technology*, Vol. II, pp. 19–31, Boca Raton, Fla. CRC Press, (1984).

Mayhew, E. and Papahadjopoulos, D. Therapeutic Applications of Liposomes. In: M. Ostro (ed.), Liposomes, pp. 289–341, New York, Marcel Dekker (1983a).

Mayhew, E., Rustum, Y. M. and Vail, W. J. Inhibition of Liver Metastasis of M5076 Tumor by Liposome-entrapped Adriamycin. Cancer Drug Delivery 1: 43–57 (1983b).

Mayhew, E. and Rustum, Y. M. Effects of liposome entrapped adriamycin (ADM) against ovarian tumor M5076 "metastatic" to the liver. Proc Am Assoc Cancer Res 23:170 (Abstract 668) (March, 1982.)

Mayhew, E., Rustum, Y. M., Szoka, F. and Papahadjopoulos, D. Role of cholesterol in enhancing the antitumor activity of 1-alpha-D-Arabinofuranosylcytosine entrapped in reverse phase evaporation vesicles. Cancer Treatment Reports 63:1923–1928 (1979).

Mihich, E., Future Perspectives for biological Response Modfifiers: A Viewpoint. Seminars in Oncol. 13: 234–254,(1986).

Myers, E., McGuire, W. and Young, R., Adriamycin: amelioration of toxicity by alpha-tocopherol. Cancer Treatment Reports 60:961–962 (1976).

Olson, F., Mayhew, E., Maslow, D., Rustum, Y. and Szoka, F. Characterization, toxicity and therapeutic efficacy of adriamycin encapulated in liposomes. Eur J Cancer Oncol 18(2):167(1982).

Oppenheim, J. J., Kovacs, E. J., Matsushima, K. and Duram, S. K. There is More Than One Interleukin-1, Immunology Today, 7: p. 45–56, (1986).

Parker, R. J., Hartman, K. P., and Sieber, S. M. Lymphocytic Absorption and Tissue Disposition of Liposome-Entrapped [$^{14}$C] Adriamycin Following Intraperitoneal Administration to Rats. Cancer Res. 41:1311-1317 (1981).

Rahman, A., Kessler, A., More, N., Sikie, B., Rowden, G., Woolley, P. and Schein, P. S. Liposomal protection of adriamycin-induced cardiotoxicity in mice. Cancer Res. 40:1532-1537 (1980).

Riccardi, C., Pucetti, P., Santoni, A., Herberman, R. B. and Bonmasser, E. Adriamycin-induced Antitumor Response in Lethally Irradiated mice. Immunopharmacology 1: 211-220 (1979).

Rogan, A. M., et al, Science 224: 994 (1984).

Salazar, D. and Cohen, S. A. Multiple Tumoricidal Effector Mechanisms Induced by Adriamycin. Cancer Res. 44: 2561-2566 (1984).

Santoni, A., Riccardi, C., Sorci, V. and Herberman, R. B. Effects of Adriamycin on the Activity of mouse Natural Killer Cells. J. Immunol. 124: 2329-2335 (1980).

Scheulen, M. E., et al, Proc Am Assoc Cancer Res. 23:992 (1983).

Sikic, B. I., et al, Science, 228:1544 (1985).

Sonneveld, P. Effect of alpha-tocopherol on the cardiotoxicity of adriamycin in the rat. Cancer Treatmnent Reports 62:1033-1036 (1978).

Stoychov, J. N., Schultz, R. M., Chirigos, M. A., Pavlidis, N. A. and goldin, A. Effects of Adriamycin and Cyclophosphamide Treatment on Induction of Macrophage Cytotoxic Function in Mice. Cancer Res. 39: 3014-3017 (1979).

Szoka, F., et al, Am. Rev. Biophys. Bioeng., 9: 467 (1980).

Tomazic, V., Ehrke, M. J. and Mihich, E. Augmentation of the Development of Immune Responses of Mice Against Allogenic Tumor Cells After Adriamycin Treatment. Cancer Res. 41: 3370-3376 (1981).

Wang, Y. M., Madanat, F. F., Kimball, J. C., Gleiser, C. A., Ali,.M. K., Kaufman, M. Q. and van Eyes, J. Effect of vitamin E against adriamycin-induced toxicity in rabbits. Cancer Res 49:1022-1027 (1980).

Weinberg, J. B., Chapman, Jr. H. A. and Hibbs, Jr. J. B. Characterization of the Effects of Endotoxin on Macrophage Tumor Cell Killing. J. Immunol. 121: 72-79, (1978).

Weiss, B., Annals NY Acad Sci 356:319 (1980).

Young, R. C., et al, N. Eng. J Med. 305:139 (1981).

BACKGROUND OF THE INVENTION

Adriamycin (ADM) is a widely used anti-tumor agent. Two possible mechanisms of ADM anti-tumor activity have been proposed. One is direct chemical interaction between the drug and the target cell DNA, to interfere with cell replication and/or gene expression.- The second is increased tumoricidal activity of lymphoid cells, such as macrophages and lymphocytes, in response to ADM administration.

Nonspecifically activated human macrophages can recognize and selectively destroy tumor cells in vitro. In studies of drug induced modulation of host defenses, cells of the monocyte-macrophage lineage are frequently identified as important mediators of pharmacological effects (Mihich; Ehrke, 1985). Other studies indicate that activated macrophages may circumvent the problem of tumor heterogeneity and that their action may not lead to the development of resistance in tumor cells (Fogler).

Increased phagocytic activity and enrichment of immature macrophages in the spleens of ADM-treated mice have been observed (Ehrke, 1982). In studies on tumor growth inhibition by ADM within the peritoneal cavity, macrophages were suggested as possible mediators of drug activity (Mantovani; Riccardi). In theory, macrophages exposed to ADM either in vitro or in vivo may inhibit tumor growth as a result of sequestration and subsequent targeted release of drug from the microphages, and/or through direct macrophage mediated tumoricidal activity. In support of the latter mechanism, it has been found that ADM elicited a population of peritoneal exudate cells (PEC) that were cytotoxic to tumor cells in the absence of measurable drug (Salazar). Further, macrophage-mediated destruction of tumor cells in vitro has been reported to be independent of target-cell resistance to ADM (Giavazzi).

Biological immunostimulators, such as cytokines and bacterial cell wall derivatives, are also capable of stimulating the tumoricidal activity of macrophages. Entrapment of such immunostimulators in lipid bilayer vesicles, i.e., liposomes, potentiates the induction of tumoricidal activity in vitro and in vivo (Hisano; Fidler). The liposome effect effects may be due to increased incorporation of the immunostimulator into macrophages and phagocytic components of the retinculoendothelial system (RES).

The encapsulation of ADM in liposomes also increases the therapeutic index of the drug in animal tumor model systems (Mayhew, 1983a, 1983b, 1984) and in neoplasms of the liver in humans (U.S. patent application for "Liposome/Anthraquinone Drug Composition and Method", Ser. No. 806,084, filed Dec. 6, 1985). The basis of this effect appears to be reduced toxicity, probably reduced cardiotoxicity (Forssen, 1979, 1981; Maslow; Olson; Rahman). In addition, alpha-tocopherol (vitamin E), which has been reported to stabilize phospholipid membranes (Diplock; Fukazawa), has also been reported to reduce the cardiotoxicity of ADM in animals when both compounds are administered in the free form (Myers; Sonnenfeld; Wang). A study reported by two of the inventors herein suggests that ADM entrapped in liposomes containing entrapped alpha-tocopherol is more effective against tumor growth in mice than is free ADM (Mayhew, 1982).

SUMMARY OF THE INVENTION

It is one general object of the invention to provide more effective anti-tumor therapeutic methods and compositions which contain liposome-encapsulated ADM in combination with secondary compounds, such as adriamycin-protective compounds or immunostimulators.

More specifically, it is one object of the invention to improve the therapeutic effectiveness of ADM by delivering the drug in a liposomal agent containing the secondary compound in coentrapped form.

Another object of the invention is to provide methods for enhancing the potentiation of host defenses by ADM.

The invention includes a method for enhancing the therapeutic effectiveness of ADM. There is provided, according to the method, a suspension of lipid bilayer vesicles containing ADM and a con-entrapped secondary compound. This suspension is administered parenterally in a therapeutically effective amount to a subject for tumor treatment.

In one embodiment, the secondary compound is a drug-protective agent which is effective to reduce the toxicity of ADM. Exemplary compounds in this class include free-radical quenchers, such as alpha-tocopherol, alpha-tocopherol succinate, N-acetylcysteine, niacin, isocitrate, and hydroxybutylated toluene. Studies in support of the present invention, and reported below, demonstrate that liposomes containing entrapped ADM and a free-radical quencher, such as alpha-tocopheral, provide a significant reduction in toxicity, as evidenced by increased $LD_{50}$ values in laboratory animals, over free ADM or liposomes containing ADM alone. The studies also indicate that liposomes containing coentrapped ADM and alpha-tocopherol give greater long-term survival in cancer-cell-injected animals than a mixed population of ADM-liposomes and alpha-tocopherol liposomes. The method is applicable particularly to treating neoplasms of the liver, by intravenous injection of the liposome suspension.

In another aspect, the secondary compound is an immunostimulator capable of potentiating the induction of cell mediated tumoricidal activity in one or more lymphoid cell types. Exemplary stimulators include cytokines and lipopolysaccharides obtained from the cell walls of gram-negative bacteria. The method is applicable particularly to treating ovarian or pancreatic tumors, by intravenous injection of the liposome suspension. Also included in this aspect of the invention is a liposome composition which is composed of liposomes containing coentrapped adriamycin and an immunostimulator.

In another aspect, the invention includes a method of enhancing the tumoricidal activity of macrophages, as evidenced by the ability of isolated macrophages to lyse mastocytoma cells in culture. The method is based on the discovery that macrophages exposed in vivo to ADM in liposomal form, and exposed to an immunostimulator, such as lipopolysaccharide (LPS), show substantially greater tumoricidal activity, and for a longer period, than macrophages similarly treated with free (non-entrapped) ADM. The method thus involves administering in vivo a suspension of liposomes with entrapped ADM, and exposing the macrophages to the immunostimulator. According to one feature of the invention, the macrophages derived from a subject after administration of the ADM liposomes can be stimulated in vitro by cell exposure to the immune stimulator, for up to at least about 18 days after initial ADM administration. The macrophages produced by this method may be reinjected into the subject for tumor treatment.

Alternatively, both the ADM liposomes and the immune stimulator can be administered in vivo, preferably in a liposomal formulation containing both ADM and the immunostimulator coentrapped in the same liposomes. Where the ADM liposomes are administered by intraperitoneal injection, the method may be used to treat ovarian tumors, which tend by metastasize by migration from the peritoneum via the lymph nodes. Cells of the monocyte-macrophage lineage present in the peritoneum and induced to increased tumoricidal activity also follow this route to the bloodstream.

These and other and features of the invention will become more fully apparent when the following detailed description of the invention is read in conjunction with the accompanying drawings.

DETAILED DESCRIPTION OF THE INVENTION

I. Preparing ADM Liposome Compositions

This section describes the component selection and liposome-processing methods for preparing the ADM liposomes for use in the present invention.

A. Lipid Components

The liposomes in the composition are formed from standard vesicle-forming lipids, which generally include neutral and negatively charged phospholipids and a sterol, such as cholesterol. The selection of lipids is guided by considerations of (a) drug-release rate in serum, (b) drug-entrapment efficiency, (c) liposome toxicity, and (d) biodistribution and targeting properties.

Considering the effect of lipid components on in vivo drug-release rates, the most important compositional factors are chain length, degree of unsaturation, and head group charge and side groups in the phospholipids. The dependence of drug release rate on lipid composition is due in part to differences in the rate of exchange of amphipathic drug with the outer liposome bilayer, and in part to the differing stability of liposomes having different lipid compositions. From earlier studies reported in U.S. patent application for "Liposome-/Anthraquinone Drug Composition and Method", Ser. No. 806,084, filed Dec. 6, 1985, now U.S. Pat. No. 4,797,285, issued Jan. 10, 1989 it has been found that negatively charged phospholipids, such as phosphatidylglycerol (PG) and phosphatidylserine (PS), tend to enhance drug liposome stability as measured by ADM release in 50% plasma, whereas cardiolipin (CL) produces a marked destabilizing effect on the liposomes. The latter effect may be related to the apparently strong interaction between ADM and cardiolipin which is reflected by drug and lipid crosslinking which also occur in vivo (Goormaghtigh). Neutral phospholipids, particularly phosphatidylcholine (PC), and negatively charged phospholipids, such as PG, PS, and phosphatidylinositol (PI), having acyl chain components of selected chain lengths and degree of saturation are available from commercial sources, or can be prepared by known techniques. Another lipid component which is important to liposome stability, and therefore to drug release rate, is cholesterol. Studies carried out in support of the above '084 patent application examined the in vitro release of ADM from liposomes whose lipid components contained varying amounts of cholesterol, PC, and PG, or PS. Briefly summarizing the results which were obtained, 20 mole percent cholesterol produces a 2-fold to 3-fold enhancement in drug retention in PC liposomes, although no additional improvement is seen up to a cholesterol mole ratio of 50%. In liposomes formed with 30 mole percent PG, good drug retention achieved in the absence of cholesterol, but progressively greater stability is observed with increasing amounts of cholesterol. PS, another negatively charged phospholipid, gives substantially the same result as found with PG. Additional studies indicate that the increased drug retention is seen over a range of negatively charged phospholipid of between about 10–40 mole percent.

Drug-entrapment efficiency, another factor to be considered in selecting a lipid composition, refers to the total amount of drug which can be loaded into liposomes, expressed as a ratio of drug per mole per liposome lipid. High entrapment efficiency is desirable both in terms of preparation costs and for maximizing the amount of drug which can be delivered in liposomal form in a give volume of liposomes. Earlier studies on the entrapment efficiency of multilamellar vesicles (MLVs), and discussed in the above '084 patent application, suggest that a negatively charged phospholipid, such as PG or PS, is required for good entrapment efficiency, whereas that cholesterol has only a minor effect, if any, on drug entrapment. With small unilamellar vesicles (e.g., SUVs), a similar increase in entrapment efficiency was observed with either PG, or PS. Also, entrapment efficiency was relatively poor when saturated phospholipids (DPPG alone or with DPPC) were substituted for the more unsaturated egg lipids, and in the predominantly very small liposomes (SUVs). Taken together, the data suggest that the optimal liposome composition, for obtaining both high entrapment efficiency and good drug retention in vitro (in serum plasma), contains between 10–40 mole percent negatively charged phospholipid, particularly PG; between 20–50 more percent cholesterol; and at least about 40 mole percent of a natural phospholipid, such as PC. Within this range of lipid components, the degree of acyl chain saturation and chain length may be varied to achieve desired drug-release characteristics in vivo, although it would be expected that a composition containing a high percentage of saturated lipids would have a reduced drug entrapment efficiency.

Another important consideration in the choice of lipid components is the toxicity of the drug/liposome composition which is produced. Since the slluble drug is generally more toxic than liposome-entrapped drug, it is desirable that the liposomes have both good entrapment efficiency and good drug retention in vivo. The lipid composition factors which effect drug retention and entrapment are discussed above. In addition, the acyl chain composition of the lipids may produce toxicity effects which are unrelated to the amount of drug present in the liposomes. It has previously been found, in the above-cited '084 patent application, that: Liposomes composed predominantly of saturated lipids, such as DPPG and DPPC, were more toxic than liposomes formed from corresponding unsaturated phospholipids. (2) Although unsaturated lipids are less toxic, they are also much more susceptible to lipid peroxidation damage on storage, and liposomes with substantial lipid oxidation damage are considerably more toxic, in terms of $LD_{50}$ values, than corresponding fresh liposomes. Also, it would be expected that lipid oxidation damage would increase toxicity in a drug/liposome composition, through decreased drug retention.

B. Therapeutic Compounds

The therapeutic compounds in the liposomes composition of the invention include adriamycin and a secondary compound which increases the therapeutic effectiveness of ADM in tumor treatment.

As defined herein, the term "adriamycin" or "ADM"-includes anthracene glycosides, such as Adriamycin (doxorubicin), daunomycin, carcinomycin, N-acetyladriamycin, N-acetyldaunomycin, rubidazone, and 5-imidodaunomycin, and the cyanomorpholino derivative of Adriamycin (Sikic). Drugs in this class are known to have anti-neoplastic effects against a variety of cancers, including acute leukemias, breast cancer, Hodgkin disease, non-Hodgkin lymphomas, and sarcomas. One primary mechanism of the drugs appears to be intercalation into DNA and DNA damage (Young, Goormaghtigh), although membrane binding (Goormaghtigh) and enzyme-catalyzed free-radical formation (Aubel-Sadron) have also been suggested as possible contributing mechanisms of drug action. The concentration of the ADM drug in the liposomes is typically between about 2–10 mole percent of the total liposome lipids.

In one embodiment, the secondary compound is a drug-protective compound which reduced the toxicity of ADM, particularly cardiotoxicity effects related to free radical reactions. Preferred drug-protective compounds include lipophilic free radical scavengers, such as alpha-tocopherol, or a pharmacologically acceptable analog or ester thereof, such as alpha-T succinate. Other suitable free radical quenchers include butylated hydroxytoluene (BHT), propyl gallate (Augustin), and their pharmacologically acceptable salts and analogs. Additional lipophilic free radical quenchers which are acceptable for parenteral administration in humans, at an effective level in liposomes, may also be used. Still other drug-protdcthve which have been shown to reduce anthracycline cardiac toxicity when administered in free form, include N-acetylcysteine (Doroshow) and niacin and isocitrate (Scheulen).

In preparing the liposomes of the invention, the drug-protective compounds are coentrapped, for example, by encapsulation or membrane binding to produce and enhance reduction in drug toxicity. Typically, alpha-tocopherol or an analogue thereof is included at a concentration of between about 0.1 to 2 mole percent total liposome lipid.

In addition to drug-protective compounds of the type just discussed, an aqueous suspension of the liposomes may advantageously included a water-soluble iron-specific chelator, such as desferal (ferrioxamine). This compound shows exceptional iron binding affinity and has been proven safe for parenteral use in humans in treating iron-storage disease and iron-poisoning. According to an important feature of the invention described in the above '084 patent application, a suspension of ADM liposomes containing a lipophilic free radical quencher, such as alpha-tocopheral, and a water-soluble iron-specific chelator, such as desferal, show significantly reduced oxidative degradation of liposome lipids and ADM over the combined protection which is provided by alpha-tocopherol or desferal alone in combination with ADM liposomes. The chelator is in molar excess of the amount of free ferric iron in the suspension, and typically between about 10–50 mM.

A second general class of compounds which may be included in ADM liposomes, for enhanced therapeutic effectiveness, are compounds which potentiate anthracycline antibiotics, such as ADM. Included in this class are agents that block calcium uptake, such as verapamil (Rogan), compounds that interfere with calcium mobilization from an intracellular store, such as 8-(N,N-diethylamino)-octyl-3,4,5-trimethoxybenzoate (TMB-8)(Juhl), or compounds that interfere with calcium binding to the protein calmodulin, such as trifluoroperazine, thioridozine, and related compounds (Weiss). These compounds would be included, at normal therapeutically effective doses, and/or maximum concentrations consistent with liposome membrane stability, in liposomes also formulated to contain ADM drug and administered in a suitable manner.

A third class of compounds which enhance the therapeutic effectiveness of ADM liposomes, when included in the liposomes, are immunostimulators which are effective to enhance the induction of host cell defenses by ADM, and more specifically the induction of tumoricidal activity of host lymphoid cells. These compounds include lymphokines, such as interferons, and more particularly, gamma interferon, which activates natural killer cells, interleukins, such as interleukin-1 (IL-1), which have been proposed as activators of macrophage and natural killer (NK) cells (Oppenheim), and tumor necrosis factor.

Mitogens, such as lipopolysaccharide (LPS) and plant lectins are also included in the class of immunostimulators. LPS refers generally to a group of large sugar polymers linked to lipid A which are derived from the cell walls of gram negative bacteria. As will be seen below, PLS produced a significant tumoricidal enhancement of ADM treated macrophages. Since lectins, which are plant proteins that bind specifically to various carbohydrate groups of lymphoid cells, are generally toxic in free form, liposomal encapsulation would provide significant improvement of compound delivery.

C. Liposome Preparation

Methods for preparing drug-containing liposome suspensions generally follow conventional liposome preparation methods, such as those reviewed by Szoka et al. In one preferred method, vesicle-forming lipids are taken up in a suitable organic solvent or solvent system, and dried in vacuo or under an inert gas to a lipid film. ADM and other lipophilic drug components are preferably included in the lipids forming the film. The concentration of drug in the lipid solution may be included in molar excess of the final maximum concentration of drug in the liposomes, to yield maximum drug entrapment in the liposomes. In particular, ADM is typically included at a mole ratio, with respect to the other lipid components making up the liposomes, of between about 2-10 mole percent.

The aqueous medium used in hydrating the dried lipid or lipid/drug is a physiologically compatible medium, and preferably pyrogen free physiological saline, such as is used for parenteral fluid replacement. The solution is mixed with any additional solute components, such as a water-soluble iron chelator, and/or a soluble secondary compound, such as a peptide immunostimulator, at a desired solute concentration. The lipids are allowed to hydrate under rapid (with shaking) or slow (without shaking) conditions. The lipids hydrate to form a suspension of multilamellar vesicles (MLVs) whose sizes range typically between about 0.5 microns to 10 microns or greater. In general, the size distribution of MLVs in the above procedure can be shifted toward smaller sizes by hydrating the lipid film more rapidly, with shaking. The liposomes contain encapsulated chelating agent, at a concentration approximately equal to the bulk aqueous phase concentration. The method is illustrated in Example 1, for the preparation of ADM liposomes (MLVs) containing entrapped alpha-tocopherol.

Alternatively, where the liposomes are prepared to contain encapsulated compound, such as a lymphokine, a liposome preparation method which yields high encapsulation efficiency may be preferred. For example, the reverse-phase evaporation method described by Szoka yields encapsulation efficiencies as high as about 50%, so that losses of the encapsulated compound, e.g., a peptide hormone, are minimized. The reverse-phase evaporation vesicles (REVs) produced by the method are predominantly oligolamellar, and have heterogeneous sizes which are largely between about 0.5 and 20 microns.

D. Liposome Sizing

The liposome suspension may be sized to achieve a selective size distribution of vesicles in a size range less than about 1 micron and preferably between about 0.05 to 0.5 microns, and most preferably between about 0.05 and 0.2 microns. The sizing serves to eliminate larger liposomes and to produce a defined size range having optimal pharmacokinetic properties.

Several techniques are available for reducing the sizes and size heterogeneity of liposomes. Sonicating a liposome suspension either by bath or probe sonication produces a progressive size reduction down to small unilamellar vesicles (SUVs) less than about 0.05 microns in size. Homogenization is another method which relies on shearing energy to fragment large liposomes into smaller ones. In a typical homogenization procedure, MLVs are recirculated through a standard emulsion homogenizer until selected liposome sizes, typically between about 0.1 and 0.5 microns, are observed. In both methods, the particle size distribution can be monitored by conventional laser-beam particle size discrimination.

Extrusion of liposomes through a small-pore polycarbonate membrane is an effective method for reducing liposome sizes down to a relatively well-defined size distribution whose average is in the range between about 0.1 and 1 micron, depending on the pore size of the membrane. Typically, the suspension is cycled through the membrane several times until the desired liposome size distribution is achieved. The liposomes may be extruded through successively smaller-pore membranes, to achieve a gradual reduction in liposome size.

Centrifugation and molecular sieve chromatography are other methods which are available for producing a liposome suspension with particle sizes below a selected threshold less than 1 micron. These two methods both involve preferential removal of larger liposomes, rather than conversion of large particles to smaller ones. Liposome yields are correspondingly reduced.

Studies aimed at determining the biodistribution and drug clearance of ADM liposomes as a function of liposome size are reported in the above '084 patent application. The study compared ADM distribution in a number of tissues at intervals up to 24 hours after intravenous (i.v.) administration of free ADM, ADM in SUVs (liposome sizes of about 0.035 and 0.08 microns) and sized MLVs (liposomes average size about 0.115 microns). The results with the larger ADM liposomes showed increased drug levels in the liver and spleen and decreased drug levels in heart, lung, intestine, kidney, and skeletal muscles, when compared with free ADM and the smaller ADM liposomes (SUVs). Another important advantage of the larger ADM liposomes is slower drug clearance in liver and spleen tissue. The drug clearance in animals which received the smaller liposomes more closely followed that of the free drug. The improved biodistribution and longer clearance times observed with the larger vesicles are observed in the liposome size range down to about 0.05 microns. Below this range, drug distribution and clearance characteristics begin to approximate those of the free drug.

For a variety of reasons, the optimal upper size limit of the liposomes is about 0.5 microns and, preferably, about 0.2 microns. First, the desired target tissue regions, such as liver sinusoids and parenchyma, spleen, and bone marrow are more accessible to liposomes smaller than about 0.2 microns. Secondly, liposomes in the 0.2 micron size range can be readily sterilized by filtration through a depth filter. Smaller vesicles also show less tendency to aggregate on storage, thus reducing a potentially serious problem when the composition is administered parenterally. Finally, liposomes which have been sized down to the submicron range show more uniform biodistribution and drug clearance characteristics, since they have more uniform sizes.

F. Removing Free Drug

Free drug, i.e., drug present in the bulk aqueous phase of the medium, is preferably removed to increase the ratio of liposome-entrapped to free drug. The drug removal is designed to reduce the final concentration of free ADM to less than about 20% and preferably, less than about 10% of the total drug present in the composition.

Several methods are available for removing free drug from a liposome suspension. Sized liposome suspension can be pelleted by high-speed centrifugation, leaving free drug and very small liposomes in the supernatant. Another method involves concentrating the suspension by ultrafiltration; then resuspending the concentrated liposomes in a drug-free replacement medium. Alternatively, gel filtration can be used to separate larger liposome particles from solute (free drug) molecules.

One preferred procedure for removing free ADM utilizes an ion-exchange resin capable of binding drug in free, but not in liposome-bound, form. The preferred resin is a cation-exchanger, since the drug is positively charged at neutral pH.

II. Reducing ADM Toxicity

In one aspect of the invention, the therapeutic effectiveness of ADM is enhanced by administering ADM in a liposome composition also containing a coentrapped compound which acts to reduce the toxicity of ADM. The reduced toxicity provides two significant advantage in ADM therapy. First, for both short-term (acute) and long-term (chronic) therapy, the drug can be administered with greater safety. This advantage is illustrated in the study reported in Example 4, which examines the $LD_{50}$ values of ADM administered as free drug, in liposomal form, or in liposomal form with coentrapped alpha-tocopherol. The results show that encapsulation in liposomes increases the ADM $LD_{50}$ for acute survival (between 3–14 days of drug administration) about 2.5-fold, and with addition of alpha-tocopherol to the liposomes, about 3.5-fold. For chronic survival (between 50–120 days of drug administration), it was observed that encapsulation in liposomes increases the ADM $LD_{50}$ again about 2.5-fold, and with addition of alpha-tocopherol to the liposomes, over 4-fold. Thus, alpha-tocopheral enhanced the protective effect achievable with liposomes alone by over 60% for both acute and chronic survival. Clinically, the reduced toxicity, at allowable clinical doses, means fewer side effects of ADM chemotherapy, such as nausea, vomiting and hair loss. This reduction in severe short-term side effects have been confirmed in clinical studies.

According to another advantage of the treatment method, it has been discovered that liposomes with coentrapped ADM and alpha-tocopheral give enhanced therapeutic effects, as measured by long-term survival after infection with cancer cells, when compared with treatment with either ADM liposomes or a combination of liposomes containing ADM alone and alpha-tocopherol alone, i.e., where the two drug agents are in different liposome populations. This enhanced therapeutic effect is illustrated by the study in Example 3, involving long-term survival (172 days after infection) in animals injected i.p. with leukemia cells, and treated with each of the three liposome compositions just mentioned. As noted, the only survivors were in the group treated with coentrapped ADM and alpha-tocopherol. The results indicate that delivering ADM and a drug-protective agent to the same cellular site (in the same liposome) provides a therapeutic advantage over delivering the ADM and drug-protective agent via liposomes to different cellular sites, i.e., in different liposomes.

The enhanced long-term survival rates observed for liposome treatment with coentrapped ADM and drug-protective agent is surprising in view of the study reported in Example 2, which examines acute therapeutic effects of drug coencapsulation in liposomes. The study reported in Example 2 indicates that at the ADM dosage where liposomes appear to give greater short-term survival times free ADM, including alpha-tocopherol in the liposomes produces no significant increase in survival times.

The data supports the concept of using liposomes to carry more than one agent simultaneously, where one of the agents is a drug and the other agent is either a drug-protective compound, such as disclosed herein, or a drug-potentiating compound which promotes the action of the drug at the site of drug delivery.

Further reduction in drug toxicity and/or greater long-term survival may be achieved by increasing the relative amount of drug protective compound in the drug-containing liposomes. The liposome compositions routinely used in the animal studies had an alpha-tocopherol to total lipid ratio of about 1:100. Using an alpha-tocopherol succinate, the ratio of alpha-tocopherol to total liposome lipids can be made much greater, preferably in the molar ratio range of 1:20 to 1:5, i.e. between about 5 and 20 mole percent alpha-tocopherol.

III. Enhanced Host Defenses

Induction of host cell defenses, and in particular, induction of tumoricidal activity of host lymphoid cells have been implicated in the antitumor effectiveness of ADM (Mantovani, 1979, Riccardi). Studies with allogenic and syngeneic tumor models have offered support to the postulate that ADM can activate macrophages in vivo (Mantovani, 1979, Riccardi, Salazar, Hisano, Stoychov, Ehrke, 1984). Investigations performed with macrophages exposed to drug in vitro have demonstrated their resistance to the direct cytotoxicity of ADM and their ability to store and subsequently release drug at levels sufficient to exert tumor cytocidal activity (Giavazzi, Haskill, Mantovani, 1977) These studies have suggested that the storage and release of drug by macrophages in ADM treated animals may be therapeutically advantageous at tumor sites with macrophage infiltration. Such redistribution of drug by the reticuloendothelial system does not preclude the concurrent induction of augmented host responses for which there is considerable experimental evidence (Ehrke, 1982, Salazar, Cohen, Santoni, and Ehrke, 1984, 1985).

Figure 1:
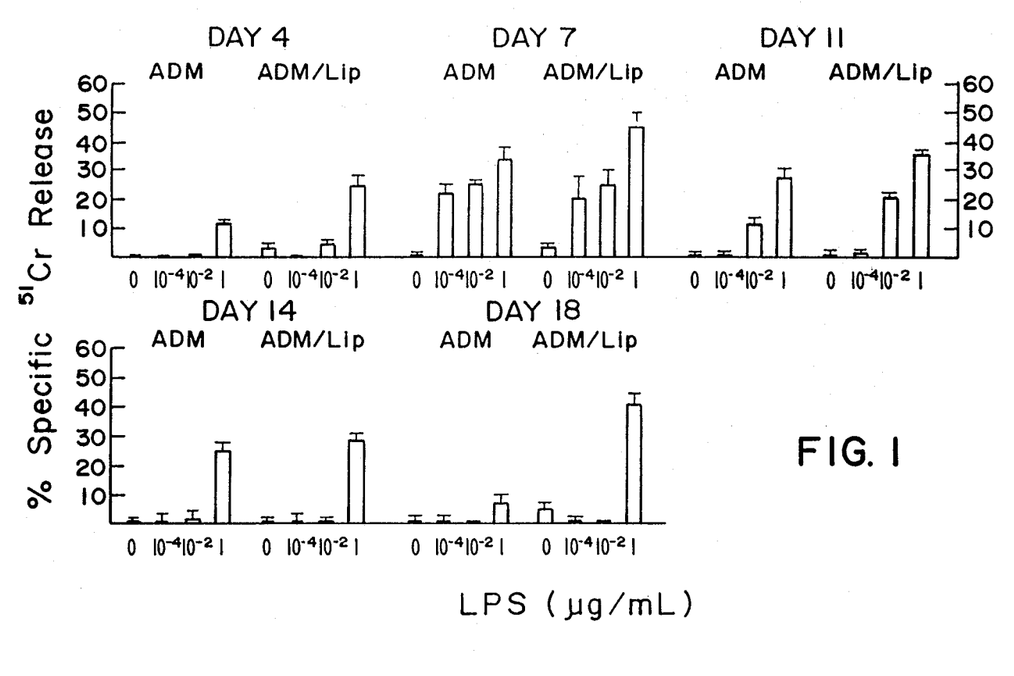
FIG. 1 shows the macrophage tumoricidal activity of adherent PECs harvested at 4, 7, 11, 14 and 18 days after intraperitoneal (i.p.) administration of free ADM or ADM liposomes, and exposed in vitro to various concentrations of lipopolysaccharide (LPS)

According to one finding of the present invention, the duration and to a lesser extent, the magnitude of macrophage activation by ADM can be enhanced significantly by ADM administration in liposomal form. One study showing the enhanced effect of ADM induction of macrophage tumoricidal activity is given in Example 5. In this study, experimental animals were given i.p. injections of free ADM or liposomal ADM, and PECs were obtained at several-day interval thereafter, as indicated in FIG. 1. The cells were further activated in culture with LPS, at the LPS concentrations indicated in the figure. Macrophage tumoricidal effect was measured by lysis of radiolabeled P815 cells, according to standard techniques. As seen from FIG. 1, tumoricidal activity was induced only in the presence of LPS, and in the early (day 4) and late (days 14 and 16), only at the highest LPS concentrations. At all time periods, induction by ADM liposomes was at least as high as and typically higher than with free ADM induction. The day 18 data in particular shows the greater duration of tumoricidal induction achieved by ADM liposomes.

The studies reported in Example 5 indicate that ADM induction of tumoricidal activity in macrophages requires additional stimulation with an immunostimulator, in the present case, LPS. Macrophages from mice treated with ADM therefore correspond to "primed macrophages" [i.e. previously exposed to a priming signal such as lymphokine and/or IFN-gamma] and require only a triggering signal such as LPS (Weinberg) for activation to occur. The immunostimulator may be administered either concurrently with ADM, in the same liposomes, or in the liposome suspension, or may be administered after ADM priming, over an activation period which is significantly longer than that induced by free ADM. In one treatment method, macrophages are induced by parenteral administration of ADM liposomes, subsequently isolated from the injected subject and activated in vitro, then reinjected into the subject.

Figure 2:
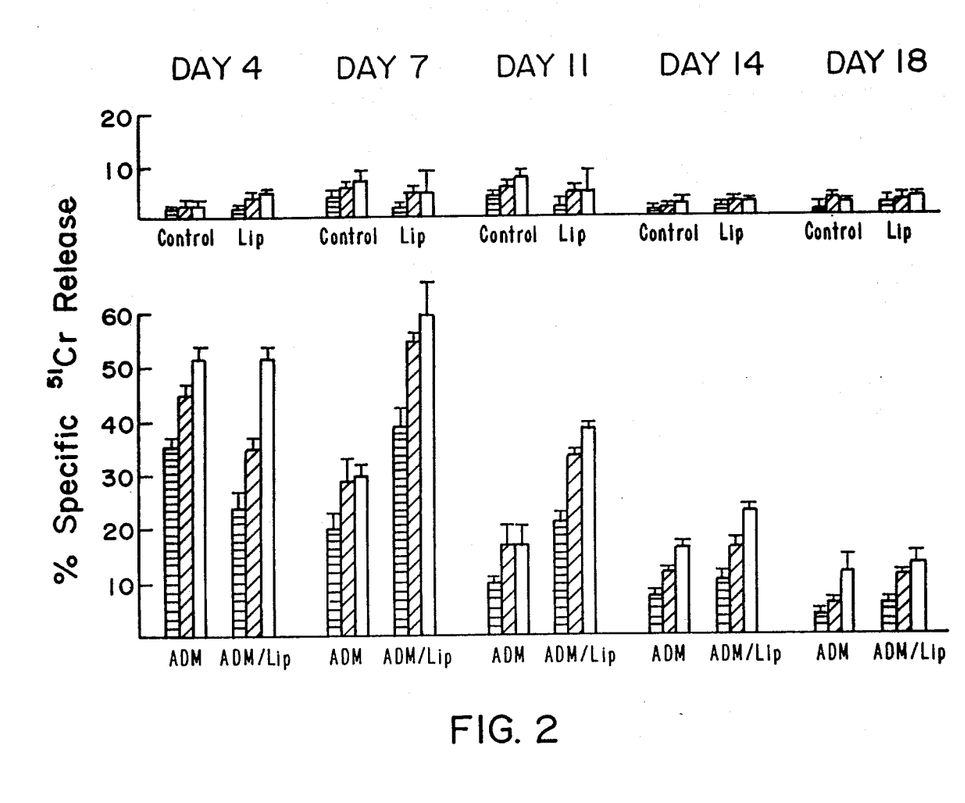
FIG. 2 shows the kinetics of drug induced effects on PEC natural killer (NK) activity against YAC-1 lymphoma cells, as measured by release of $^{51}Cr$ from the cultured tumor cells, using PEC harvested 4, 7, 11, 14, and 18 days after i.p. after administration of empty liposomes, free ADM, or ADM liposomes.

Another feature of ADM induction of host defenses is increased natural killer (NK) activity, generally associated with cytotoxic T lymphocytes. NK activity can be assayed by tumoricidal activity against YAC-1 cells (a lymphoma of A/Sn origin), which are susceptible to lysis by cells associated with NK activity, in contrast to P815 cells which are susceptible to macrophage activity only. Studies to determine enhancement of NK activity in PECs from ADM-treated animals are reported in Example 6. FIG. 2 shows tumoricidal activity of PECs taken from treated animals at the time periods indicated, following drug treatment. Neither control (untreated) or empty liposome treatment gave levels significantly above background.

The greater enhancement of NK activity which is achieved when ADM is administered in liposomal form is seen from the data in the lower portion of FIG. 2, which compares tumoricidal activity induced by free ADM or ADM liposomes at various times after drug treatment. As seen, NK activity induced by ADM liposomes was nearly twice that induced by free ADM at 7 and 11 days post drug treatment. The data presented in Table 3 in Example 6 show that the NK activity in the induced PECs is dependent on asilao GM1 antigen, confirming that the anti-YAC-1 activity is due to NK activity.

Figure 3:
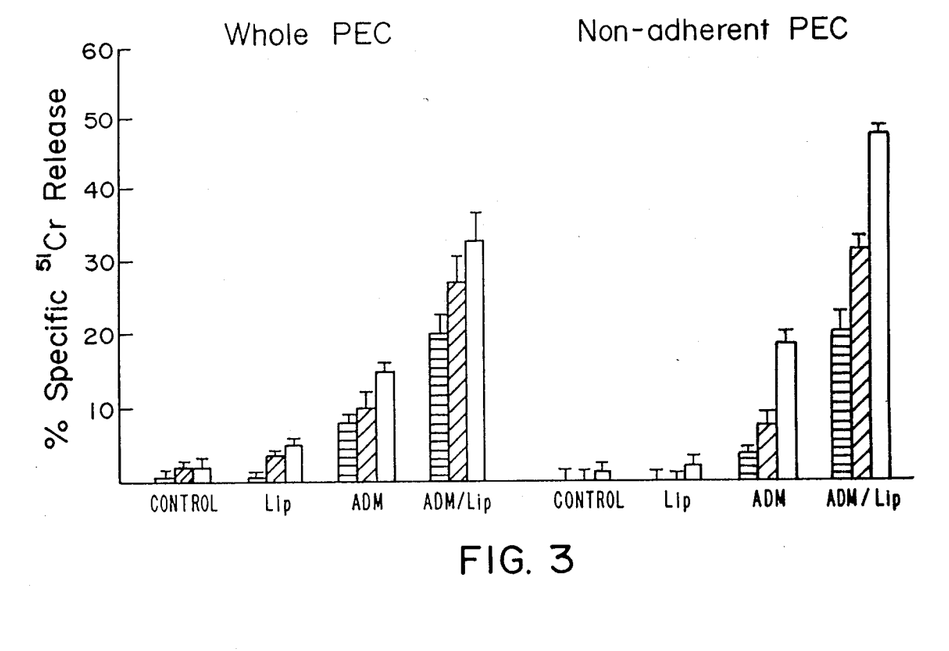
FIG. 3 shows NK activity in PEC harvested 7 days after i.p. treatment with empty liposomes, free ADM or ADM liposomes, for total PEC and non-adherent PEC.

Since both macrophages and lyophocytes may have NK activity, it was of interest to examine ADM-induced NK activity in both whole PECs (which contain both adherent, predominantly macrophage cells, and non-adherent cells), and the non-adherent, largely lymphocytic cells. The results, measured in cells obtained 7 days following drug treatment, are shown in FIG. 3. As seen, the greater induction seen with ADM liposome treatment is even more pronounced in non-adherent cells.

To determine if the enhanced macrophage tumoricidal activity or NK activity observed with ADM liposome treatment correlates with either IL-1 or IL-2 production by induced cells, these factors were assayed in PECs obtained from drug-treated animals, at 7 days post treatment. The results, given in Table 4 in Example 7, show that LPS stimulation is required for IL-1 production in cells from animals treated with ADM liposomes. By contrast, IL-1 production in PECs from animals treated with free ADM was substantially independent of LPS activation, and about as high as the highest levels seen in the PECs from ADM liposome treatment. IL-2 activity in the cells was about background, with or without LP activation, for both free ADM and ADM liposome treatment. There is thus no simple correlation between IL-1 levels in the induced macrophages and NK cells and the enhanced tumoricidal activity seen with ADM liposome treatment.

The possibility that the extension in the duration or magnitude of augmented PEC macrophage and NK activities, respectively, may be due to a persistence of intra- and/or extra-cellular ADM in the peritoneal environment following drug treatment with liposomes was also investigated. PEC ADM content following i.p. administration of free ADM and ADM liposomes were determined as described in Example 8, with the results shown in Table 5 there Given the relatively low levels of ADM detected in cells at 11 days, it is unlikely that cellular ADM is an important factor in macrophage of NK cell tumoricidal activity, particularly in cells obtained 18 days after drug treatment. Furthermore, cytolytic activity was not observed with macrophages from drug pretreated mice, on any of the days tested, without LPS stimulation. Even if one were to postulate that LPS stimulation elicits ADM release from macrophages, this should not have been a factor since the assay procedure included washing between the LPS stimulation and addition of radiolabeled P815 target cells. Finally, the fact that PEC cytolytic activity was lower on day 4 than for day 7 also argues against direct drug transfer as a mechanism and suggests that the effects at later time points (day 7, 11, 14, 18) are due to earlier ADM interactions with host defenses.

The depressed splenic NK activity observed following ADM or ADM liposomes treatment (Example 9) may represent an immunomodulation by activated macrophages in the spleen. Removal of nylon wool adherent spleen cells from the effector cell population has been shown to reverse this suppression (Santoni). While the mechanism of this macrophage mediated suppression has not been proven. It may involve cyclooxygenase metabolites such as $PGE_2$ which have been found to be elevated in spleen cells from ADM treated mice (Ehrke, 1986). In studies performed in support of the present invention, the observed suppression of splenic NK was transient in both ADM and ADM liposomes treated mice.

IV. Therapeutic Uses in Tumor Treatment

Earlier studies, discussed above, have shown that small, drug-carrying liposomes can concentrate liposome-associated drug in tissue regions, such as liver sinusoids and parenchyma, spleen, and bone marrow which are accessible to small liposomes (less than about 0.2 microns in size). These findings having important implications for ADM treatment of metastatic diseases of the liver, primary hepatomas, lymphoid proliferative diseases, and leukemias, all of which are major cancers, both in terms of numbers and geographic distribution.

The findings presented in this application indicate a further advantage of liposomal delivery of ADM, namely that the toxicity effects of ADM can be further reduced significantly (up to 60% or more) by coentrapment of a drug-protective compound, such as alpha-tocopheral, in the liposomes. In addition, either through reduced toxicity, or because of direct long-term drug effects, liposomes containing coentrapped ADM and drug-protective agent provide greater survival in animals injected with cancer cells, than when the two drug agents are administered in separated liposome populations.

Clinical trials using liposomes with coentrapped ADM and alpha-tocopherol, with i.v. administration, are in progress. ADM doses are between about 20–100 mg per patient dose, with one or more doses being given over a several week treatment period. The findings to date indicate a significant improvement in overall patient comfort, due to virtually complete elimination of gastrointestinal toxicity (nausea, vomiting, diarrhea, and stomatitis), significantly reduced incidence of alopecia, and no pain at the site of injection. The results represent a major improvement in treatment of certain cancers with ADM.

Another therapeutic application is in the treatment of ovarian and pancreatic cancers, by i.p. administration. When ADM liposomes are administered i.p., the liposomes leave the peritoneal cavity via the lymphatics and are retained in the lymph nodes (Parker). Since in metastatic ovarian or pancreatic cancer, these regional lymphatics often become occluded with tumor, administration of ADM liposomes allows for increased ADM uptake by RES cells, and would therefore result in creased drug accumulation in the regional lymphatics, and greater induction of tumoricidal activity of the cells. The liposomes preferably are formulated to contain ADM and an immuhostimulator, such as LPS, to enhance host defenses against the tumor cells. Drug dosage are in the general range given above for i.v. administration.

From the foregoing, it can be appreciated how various objects and features of the invention are met. The novel liposome composition provides codelivery of ADM and a secondary compound to a cellular site, so that the sites of ADM uptake by tumor and/or lymphoid cells, are also sites of delivery of the secondary drug. This codelivery enhances the interaction between ADM and the secondary drug at the target site, as evidenced, for example, by the greater survival of cancerous animals to codelivered ADM and alpha-tocopherol. Where the secondary drug is an immunostimulant, the codelivery insures that those RES cells which take up liposomal drug also are exposed to the immunostimulator.

The following examples, which describe various therapeutic compositions and features of the invention, are intended to illustrate, but not limit, the invention.

Materials and Cells

Phospholipids and purified cholesterol were prepared as described previously (Konigs). ADM (adriamycin) was obtained from Adria Corp. (Columbus, Ohio). Other agents used were: Lipopolysaccharide (LPS) - E. Coli strain 0111: B4 (Difco Labs, Detroit, Mich.). Interleukin 2 (IL-2, LOT 81–1232, Collaborative Research, Inc., Waltham, Mass.); Anti Asialo DM1 antisera (Wako Chem., Dallas, Tex.); Low-Tox-M Rabbit Complement (Accurate Chem., Wesbury, N.Y.), Phytohaemagglutin (PHA) (Wellcome Lab., Beckenham, England), 2-mercaptoethanol (Eastman Kodak Co., Rochester, N.Y.).

RPMI 1640 medium was supplemented with 10% fetal calf serum (FCS) (Hyclone Lab., Logan Utah), 25 mH Hepes Buffer (research Organics, Cleveland, Ohio) and 50 g/ml gentamycin (Gibco- Labs., Grand Island, N.Y.). This media was used to maintain cell lines and for experimental cultures and essays, as reported in Examples 5–9.

YAC-1 (a lymphoma of A/Sn origin) and P815 (a mastocytoma of DBA/2 origin) were maintained as continuous cultures. For cytolytic assays, tumor cells ($5 \times 10^6/0.1$ ml) were incubated with 0.1 mCi of $Na_2$ $^{51}CrO_4$ (specific activity 250–500 uCi/ug chromium) (Amersham, Arlington Heights, Ill.) for 30–45 minutes, washed 3 times and viable cells counted.

EXAMPLE 1

Preparing ADM and ADM-aT Liposomes

Multilamellar liposomes (MLVs) were made by first mixing 60 umoles of a 1:4:4 molar ratio mixture of phosphatidylglycerol: phophatidylcholine and cholesterol (in chloroform) with 1.5 mg ADM (in methanol) and 0.6 moles alpha-tocopherol (a-T) (in chloroform). The ADM-containing lipid mixture was evaporated by a rotary evaporation at room temperature. Phosphate buffered saline free of calcium and magnesium (PBS), pH 7.4 was added (1 ml/60 moles lipid) at 37° C. and the suspension was shaken at 37° overnight. The heterogeneous multilamellar liposome suspension which formed was extruded through either a 0.4 micron (Examples 2–4) or 0.2 micron (Example 5–9) nucleopore filter under 40–80 psi nitrogen pressure at room temperature and centrifuged at 130,000$\times$g for 1 hr at 20° C. to concentrate the liposomes and to remove much of the nonentrapped ADM.

The liposomes were extensively dialyzed against 100–200 volumes of PBS with stirring at 37° C. The percent of ADM entrapped, determined by fluorescence spectrophotometry, was between about 65% and 70%. The calculated molar ratio of alpha-tocopherol to total lipids in the liposomes is about 1:100. Substantially all of the alpha-tocopherol was trapped in the liposomes. The same procedure was used to prepare liposomes entrapping ADM but containing no alpha-tocopherol (by omitting alpha-tocopherol from the preparation) as described previously (Olson).

EXAMPLE 2

Acute Therapeutic Effect of ADM and ADM-aT Liposomes

The therapeutic effects of liposome ADM formulations were tested using DBA 2J mice injected intraperitoneally with $10^6$ L1210 leukemia cells. The animals were treated one day later by intravenous injection of ADM, either in the form of free ADM, liposomes entrapping ADM only (ADM(s) liposomes), or liposomes entrapping both ADM and alpha-tocopherol (ADM-aT liposomes). The dosages of ADM administered, expressed in milligrams ADM per kilogram animal body weight, are given at the left in Table 1 below. The day of death of the animals was recorded, and the mean survival time of each group was calculated. Each group contained from between 6 and 10 mice. The mean survival time and calculated standard deviations are shown at the three columns at the right in Table 1.

TABLE 1

| dose ADM (mg/kg) | Mean Survival Time (days) ± S.D. | | |
|---|---|---|---|
| | free ADM | ADM(s) liposomes | ADM-aT liposomes |
| 0 | 7.2 ± 0.4 | — | — |
| 10 | 18.4 ± 1.8 | 16.8 ± 2.4 | 17.6 ± 3.0 |
| 20 | 12.2 ± 1.6 | 17.6 ± 2.0 | 16.8 ± 1.6 |
| 50 | — | 13.0 ± 4.3 | 17.0 ± 4.0 |

The data in Table 1 show that at a dosage of 10 mg/kg, the anti-leukemic effectiveness of free ADM was maintained, but not improved, by entrapment in liposomes alone or liposomes containing alpha-tocopherol. At the 20 mg/kg dosage level, the effectiveness of liposome-entrapped ADM, either in the presence or absence of alpha-tocopherol was better than that of free ADM at the same concentration, similar to what has been reported (Mayhew, 1982). However, at no ADM dosage level was the effectiveness of ADM entrapped in liposomes, either in the presence or absence of alpha-tocopherol, greater than the optimal, 10 mg/kg dosage level of free ADM.

EXAMPLE 3

Lon-term Therapeutic Effects of ADM and ADM-aT Liposomes

Studies similar to those described in Example 2 were conducted to determine the effect of the various ADM formulations on long-term survival in mice which had been injected intraperitoneally with $10^5$ L1210 leukemia cells. The infected animals were treated with intraperitoneal injections of ADM (10 mg/kg body weight) administered either as free ADMs, liposomes, ADM-aT liposomes, or a mixed population of liposomes containing ADM only and liposomes containing alpha-tocopherol only. Significantly, the only ADM formulation that gave long-term survival (2 of 6 mice survived to 172 days after initial infection) was the liposome formulation containing coentrapped ADM and alpha-tocopherol.

At least under certain therapeutic conditions, then, supplying the drug and drug-protective compound in the same liposome population produced therapeutic results which are superior to those obtained by administering the drug and drug-protective compound in separate liposome populations. The results indicate that release of ADM and a drug-protective compound, e.g., alpha tocopherol, in the same localized liposome-target region is improves the therapeutic result over that obtainable with a mixed population of liposomes.

EXAMPLE 4

Toxicity of ADM(s) and ADM-aT Liposomes

The toxicity of the three ADM preparations in Table 1 above was tested against healthy DMA 2J mice. Groups of mice (6–10 mice/group) were injected with a single i.v. dose of free ADM, ADM(s) liposomes, and ADM-aT liposomes in doses of 2, 5, 10, 15, 20, 25, 30, 50, 75, 100 mg ADM per kg animal body weight.

It was found that the mice died at two distinct time periods after administration: within 3–14 days, and between approximately 8–12 weeks after drug administration. The data are expressed in terms of LD50, i.e. the dosage (in mg drug per kilogram of animal body weight) which produces death in half the animals receiving the drug. The upper row in Table 2 gives the LD50 data for mice dying within 14 days after drug administration (acute), the lower row, for mice dying between 50 and 120 days after drug administration (chronic). The number of mice available for determination of chronic toxicity (survival of acute toxicity) varied from between about 2 and 10 mice per group.

TABLE 2

| | Mean LD$_{50}$ (mg/kg) ± S.D. | | |
|---|---|---|---|
| | free ADM | ADM(s) liposomes | ADM-aT liposomes |
| acute | 20 ± 5 | 45 ± 5 | >75 |
| chronic | 12 ± 5 | 30 ± 5 | 50 |

The data in Table 2 confirm that both acute and chronic toxicity of ADM are reduced more than 2-fold by encapsulating the drug alone in liposomes (no alpha-tocopherol), as has been reported previously. According to an important finding of the present invention, entrapping the drug in liposomes which also contain entrapped alpha-tocopherol further reduces acute and chronic toxicity more than about 60% with respect to liposomes entrapping ADM alone. It is noted that 75 mg/kg is about the highest drug dosage which could be administered with a single intravenous injection. Therefore the LD$_{50}$ value for acute toxicity from ADM-aT liposomes may be somewhat higher than shown.

EXAMPLE 5

The Effect of ADM liposomes on Macrophage Tumoricidal Activity

Female C57BL/6Cr 6 weeks old were obtained from the Goodwin Institute for Cancer Research, Plantation, Fla. and Jackson Laboratory, Bar Harbor, Me. respectively.

A. Drug Administration

A dose of 10 mg/kg of free or encapsulated ADM was administered intraperitoneally (i.p.) to C57BL/6N mice. ADM concentration in liposomes was determined after chloroform/methanol extraction by fluorescence at excitation 468 nm, emission 585 nm. The ADM concentration was determined from standard curves. Between 50–60% of the initial starting concentration of ADM was entrapped in liposomes in different preparations resulting in 12–18 µg of ADM/umole of lipid. An equivalent quantity of liposomes (~300 umoles/kg) alone was injected i.p. in liposome controls. All injections were done using the same vol./wt./ratio. B. Macrophage Tumoricidal Activity This assay for macrophage tumoricidal activity is based on the specific tumoricidal activity of macrophages against P815, a mastocytoma of DBA/2 origin.

Peritoneal Exudate Cells (PEC) were obtained from the injected mice at 4, 7, 11, 14, and 18 days following ADM and/or liposome administration. The peritoneal cavity was lavaged with 7 ml of ice cold Hank's Balanced Saline solution (pH 7.4 Gibco, Chagrin Falls, Ohio) using a 10 ml syringe and 22 gauge needle. PEC from at least six mice were pooled, centrifuged at 300×g at 4 C. for 5 min and resuspended in culture media. Viable cells, by trypan blue exclusion, were counted on a hemacytometer in all assays. In general, PEC prepared as indicated were found to be about 90% viable. The total numbers of cells (PEC) recovered from normal control mice ranged between 2 and $5 \times 10^6$ per mouse.

For cytotoxic macrophage assays, 0.1 ml aliquots of PEC suspensions ($1.25 \times 10^6$ cells/ml) were dispensed into the wells of flat bottom, 96 well, microwell plates (Costar, Cambridge, Mass.). The cells were allowed to adhere during a 24 h incubation and then the plates were washed three times with warm media to remove non-adherent PEC. These adherent PEC monolayers [90% macrophages by morphology and nonspecific esterase, as determined by (Sigma Diagnostic Kit, Sigma Chem (St. Louis, Mo.) were incubated for 18 h with or without LPS in a total volume of 0.2 ml. The macrophage monolayers were then washed and $10^4$ radiolabeled P815 cells were added to each well in a final volume of 0.2 ml. After an 18 h incubation the plates were centrifuged at 300×g for 5 min. All incubations were carried out at 37° C. in a humidified atmosphere containing 5% $CO_2$.

A 0.1 ml volume of supernatant was removed from each well and $^{51}Cr$ release was determined in a gamma counter (model 1197, Searle Analytic Inc., Des Plaines, Ill.).

In all assays of lytic activity, including those given in Examples 6 and 7 below, the percent specific $^{51}Cr$-release was determined using the following formula:

$$\% \text{ Specific Release} = \frac{\text{Exp. Release} - SR}{MR - SR} \times 100$$

The spontaneous release (SR) was determined by incubating $^{51}Cr$-labeled target cells with nonactivated, adherent resident PEC for 18 h. Spontaneous release was 18-24% in 18 h assays. Maximum releasable (MR) label was determined by adding 0.1 ml of 1% Triton X-100 to $10^4$ labeled target cells in 0.1 ml.

The specific release data calculated as above is shown in FIG. 1, which gives percent release for macrophages derived from animals treated with ADM or ADM liposomes, and harvested at 4, 7, 11, 14, or 18 days after drug administration. The abscissa in each bar graph shows increasing concentrations of LPS which were added to the cell cultures. In all treatment groups, only background activity (0-8% specific $^{51}Cr$ release) was observed with adherent PEC cultures without LPS addition.

As seen from FIG. 1, LPS-stimulated cytolysis of P815 cells by control or liposome-control PEC was at background levels throughout (data not shown) while drug treated groups had elevated activity day 4 through day 18. Only macrophages from animals stimulated with ADM liposomes and exposed to LPS (1.0 μg/ml) displayed significant macrophage tumoricidal activity 18 days after treatment, and ADM liposomes produced greater tumoricidal activity at all time points. This was a consistent finding observed in a total of 3 separate experiments. Macrophage activation at lower LPS concentrations ($10^{-4}$–$10^{-2}$ g/ml) was greatest on day 7 regardless of the mode of ADM administration.

EXAMPLE 6

ADM Effect on Lymphocyte Tumoricidal Activity

Total cultured PEC, including both adherent and non-adherent cells, and non-adherent cells only were assayed for natural killer (NK) activity, based on the specific tumoricidal activity of lyophocytes against YAC-1, a lymphoma of A/Sn origin.

A. total PEC

The procedures employed in Example 5 for administering liposomes and/or ADM, and isolating and culturing PEC were followed.

For cytotoxic Natural Killer (NK) assays, PEC, at various concentrations, were plated in round bottom microwell plates (Linbro, Flow Labs, McLean, VA) in a volume of 0.1 ml and $10^4$ radiolabeled YAC-1 cells were added in 0.1 ml. The final cell mixtures contained a ratio of exudate to tumor cells of 12.5:1, 25:1, or 50:1. After the addition of YAC-1 target cells, the plates were incubated for 4 h, followed by centrifugation, and counting of 0.1 ml of supernatant as above.

Lytic activity, expressed as a percent specific 51Cr release, was determined as above. The spontaneous release (SR) was determined by incubating $^{51}Cr$-labeled target cells alone for 4 h. Maximum releasable (MR) label was determined by adding 0.1 ml of 1% Triton X-100 to $10^4$ labeled target cells in 0.1 ml.

The data presented in FIG. 2 show the kinetics of specific $^{51}$ release, for control, empty liposome, free ADM and ADM liposome administration. The three bars in each group represent exudate:tumor cell ratios of 12.5:1 (horizontal cross hatching, at the let in each group), 25:1 (oblique cross hatching, at the center in each group), and 50:1 (empty bars, at the right in each group). The release levels seen at the top in FIG. 2 indicate that liposomes alone have essentially no lymphocyte induction effect. The data shown at the bottom in FIG. 2 demonstrate the greater levels of lymphocyte NK activity, achieved when ADM is administered in liposome entrapped form. These differences are. most striking at day 7 and day 11, where NK activity induced by ADM liposome treatment is nearly twice that induced by free ADM, at all three ratios of exudate:tumor cells.

B. Effect on NK Activity of Anti-Asialo GM1 Antibody

In order to verify that the effector cells in the PEC population that were active against YAC-1 cells had.NK properties, PECs were treated with anti-Asialo GMl antiserum and complement in vitro prior to the 4 hr toxicity assay for PECs. The PECs were obtained 7 days after control, empty liposomes, free ADM, and ADM liposomes treatment, as above.

Anti-Asialo GM1 antibody was added directly to PEC in the microwells at a final dilution of 1:20. After 30 min on ice the cultured effector cells were spun down, supernatant removed and the cells resuspended. Low toxicity rabbit complement was added (final dilution 1:20) and the cultures incubated for 45 min. After 3 washings, the PECs ($5 \times 10^5$) were cultures with $10^4$ radio-labeled YAC-1 cells, and radioactivity released was assayed after 4 hours. As seen from the data in Table 3, complement plus antibody abrogated NK activity, confirming that the anti-YAC-1 activity in the PECs is due to NK activity.

TABLE 3

| | In Vitro Treatment | |
|---|---|---|
| PEC Population | Untreated | Asialo GM$_1$ Antibody + Complement$^C$ |
| Exp. No. 1 | | |
| Control | 2.5 ± 1.0 | 3.0 ± 0.9 |
| Lip-Control | 4.8 ± 0.4 | 0.8 ± 0.9 |
| ADM | 16.9 ± 2.6$^d$ | 3.4 ± 0.9 |
| ADM/Lip | 37.1 ± 2.2$^{d,e}$ | 4.8 ± 0.2 |
| Exp. No. 2 | | |
| Control | 0.7 ± 2.0 | 0 |
| Lip-Control | 2.1 ± 2.1 | 0 |
| ADM | 18.9 ± 1.4$^d$ | 0.2 ± 0.8 |
| ADM/Lip | 34.9 ± 0.9$^{d,e}$ | 0.8 ± 0.9 |

C. Non-adherent PEC

Since Asialo GM1 antigen can be expressed on certain subsets of macrophages (predominantly in the adherent PEC fraction), a population of PECs depleted of macrophages by plastic adherence was assayed in parallel with corresponding whole PEC populations. For preparation of nonadherent PEC, 3.4 ml aliquots of PEC suspension ($1.25 \times 10^6$ wells/ml) were incubated in wells of 6 well cluster dishes (Costar, Cambridge, MA). After a 24 h incubation, the nonadherent cells pooled from a total of three washes were counted and used. This procedure resulted in the recovery of 25–30% of originally cultured PEC.

The cells were mixed with YAC-1 cells, and assayed for NK activity as above. FIG. 3 shows the measured NK activity for total and non-adherent PEC 7 days after treatment, for control, empty liposome, free ADM, and ADM liposomes. The three bars in each group in the figure represent the same exudate to tumor ratios as in FIG. 2. Consistent with the properties of NK cells, the PEC-NK activity of the nonadherent effector cells was similar to that of the whole effector cell populations, with the overall pattern of activities being the same. The results from parts B and C herein show that the drug-induced PEC-NK activities have characteristics ascribed to non-induced natural killer cells, i.e., they are sensitive to anti-Asialo GM1 antibody lysis, and they are associated with lymphocyte cells.

EXAMPLE 7

IL-1 Like Activity of PEC Culture Supernatant

This section examines levels of IL-1 and IL-2 which are produced in cultures of adherent PEC cells obtained from animals 7 days after treatment with free ADM or ADM liposomes. The purpose is to determine if the enhanced macrophage tumoricidal activity and NK activity detailed above correlates with increases in either IL-1 or IL-2.

PECs were obtained as above 7 days after administration of empty liposomes, free ADM, or ADM liposomes. The cells were cultured for 18 hours with the concentrations of LPS indicated below in Table 4.

A standard thymocyte comitogenic assay for IL-1 was used to test 18 h adherent PEC culture supernatants for IL1 like activity. Thymopytes ($5 \times 10^5$) from C3H/Hej mice were added in 0.1 ml/well to flat bottom, 96 well plates. An equal volume of adherent PEC culture supernatant was added for a final volume of 0.2 ml. To facilitate a proliferative response, the media was supplemented with PHA (0.8 g/ml) and 2-mercaptoethanol ($2.5 \times 10^5$M). Cultures were incubated for 72 h. Four hours before harvesting, the cultures were pulsed with [$^3$H]dThd (New England Nuclear, 2 Ci/mole; 1 Ci/50 1/well).

Cells were harvested on glass fiber filters with an Otto Hiller cell harvester. The radioactivity was measured by scintillation counting using a Beckmann counter (Model LS 7000). Thymidine uptake by the thymocytes was expressed as mean cpm±S.D.

The procedure used for assaying IL-2 has been described (Ehrke, 1986). Briefly, using a long term, IL-2 dependent cytolytic T cell line (CTCL-1), $10^4$ cells in 0.1 ml were added to 0.1 ml volumes of conditioned media from adherent PEC cultures. The cells were incubated for 24 h and pulsed with [$^3$H]Thd (1 Ci/well) 4 h before harvest. Results were expressed as the arithmetic mean of cpm dThd uptake ±S.D. A semipurified, rat IL-2 preparation was used as a positive control.

Table 4 below shows the measured IL-1 and IL-2 activities. As seen, control and empty liposome control PEC supernatants had detectable IL-1-like activity only following stimulation of the cells with the highest tested LPS concentration (1,000 ng/m). In cultures without LPS stimulation, only free ADM PEC released factor(s) with IL-1 activity into cell free supernatants. Supernatants from both ADM and ADM liposomes had IL-1-like activity following stimulation with LPS at concentrations ranging from 0.001 to 1,000 ng/ml. While the elaboration of IL-1-like activity from ADM liposomes PEC was dependent on the concentration of LPS, no significant increase in this activity from ADM PEC was observed with LPS exposure

TABLE 4

| | Control | Lip | ADM | ADM/Lip |
|---|---|---|---|---|
| IL-1$^b$ | | | | |
| LPS (ng/ml) | | | | |
| 0 | 2226 ± 405 | 1930 ± 185 | 9142 ± 1179$^f$ | 2942 ± 534$^g$ |
| 1000 | 4821 ± 1096$^e$ | 5120 ± 1520 | 10598 ± 831$^f$ | 12826 ± 270$^{e/g}$ |
| 10 | 2653 ± 452 | 2492 ± 226 | 10446 ± 226$^f$ | 8140 ± 711 |
| 0.1 | 2262 ± 319 | 2218 ± 567 | 11588 ± 953$^f$ | 55552 ± 483$^e$ |
| 0.001 | 2240 ± 582± | 1961 ± 138 | 9693 ± 230$^f$ | 4720 ± 599 |
| IL-2$^c$ | | | | |
| 0 | 224 ± 31 | 577 ± 113 | 285 ± 86 | 253 ± 53 |
| 0.001–1000$^d$ | 321 ± 61 | 290 ± 51 | 286 ± 74 | 205 ± 52 |

EXAMPLE 8

PEC ADM Content

PECs obtained at 4, 7, and 11 days after administration with empty liposomes, free ADM, or ADM liposomes were assayed for ADM concentration. ADM was extracted from $10^6$ PEC/sample by sonication in 36.5% HCl: absolute ethanol (1:11) in an ice bath for 5 min. This sonicated lysate was centrifuged (12,150×g) for 20 min at 4–6 C. The supernatant was measured for fluorescence at 468 nm excitation and 585 nm emission using a Perkin-Elmer (Model 650–10S) spectrofluorometer.

The data shown in Table 5 below are expressed in terms of ng ADM/$10^6$ PECs. As seen, slight fluorescence was detectable 4 and 7 days after free drug administration. Increased levels of fluorescence were observed in ADM liposomes on days 4 and 7 but by day 11, although some fluorescence was still detected, the level was no statistically significantly greater than that of the control PEC.

TABLE 5

| Treatment | ADM Equivalents in PEC[a] | | |
|---|---|---|---|
| | Day | Day 7 | Day 11 |
| Lip | $0.2 \pm 0.3$[b] | $0.2 \pm 0.2$ | $0.3 \pm 0.3$ |
| ADM | $4.2 \pm 0.5$ | $1.4 \pm 0.4$ | $0.2 \pm 0.2$ |
| ADM/Lip | $14.4 \pm 6.2$ | $3.5 \pm 1.5$ | $2.1 \pm 2.5$ |

EXAMPLE 9

Splenic NK Activity

Animals were treated with empty liposomes, free ADM, or ADM liposomes as in Example 5. Spleens were aseptically removed on the day of sacrifice, at 4, 7, and 11 days after drug treatment, and single cell suspensions were prepared by passage through coarse (50 mesh) and fine (200 mesh) stainless steel gauze, as described previously ((Tomazic). Viable cells, by trypan blue exclusion, were counted on a hemacytometer in all assays. In general, spleen cell populations prepared as indicated were found to be about 95% viable. The total numbers of cells recovered from normal control mice ranged between 4 and $6 \times 10^7$ per mouse for spleen cells.

Figure 4:
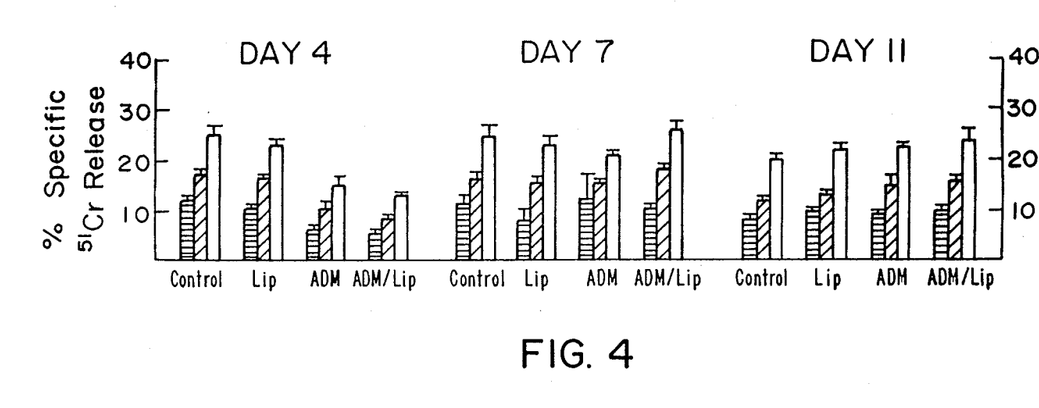
FIG. 4 shows the effect of i.p. administration of empty liposomes, free ADM, and ADM liposomes on NK activity in spleen cells.

Fresh spleen cells were added to $^{51}$Cr labeled YAC-1 cells at different effector to target cell ratios. Specific release of $^{51}$Cr from the tumor cells was determined as in Example 6, with the results shown in FIG. 4. Splenic activity was reduced in both free ADM and ADM liposome groups in 4 days following treatment. The suppression was not observed following treatment 7 or 11 days before sacrifice, suggesting that this effect on splenic NK was transient.

While the present invitation has been illustrated with respect to one particular embodiment, it will be appreciated by those skilled in the art that various changes and modifications can be made without departing from the scope and spirit of the invention.

What is claimed is:

1. In the treatment of cancerous tumors in a mammal in need of such treatment, a method for enhancing the therapeutic effectiveness of adriamycin and a secondary compound capable of:

(a) reducing adriamycin toxicity; or (b) enhancing the induction of host defenses by adriamycin, when administered in free form, comprising providing a suspension of lipid bilayer vesicles containing co-entrapped adriamycin and the secondary compound, and administering a therapeutically effective amount of the suspension parenterally.

2. The method of claim 1, wherein the secondary compound acts to reduce the toxicity of adriamycin, and is selected from the group consisting of alpha-tocopherol, including analogues thereof, including alpha-tocopherol succinate, provided that if the secondary compound is alpha-tocopherol, the toxicity for adriamycin is reduced at least three and a half times.

3. The method of claim 2, wherein the compound includes alpha-tocopherol, and the toxicity of the drug entrapped in lipid vesicles also containing alpha-tocopherol, as measured in mice, is decreased at least about 50% below the toxicity of the same amount of adriamycin administered in liposomes which do not contain alpha-tocopherol.

4. The method of claim 2, wherein the liposomes also contain a secondary compound capable of enhancing the induction of host defenses by adriamycin.

5. The method of claim 1 wherein the secondary compound is an immunostimulator which potentiates the induction of tumoricidal activity in lymphoid cells.

6. The method of claim 5, wherein the immunostimulator is selected from the group consisting of lipopolysaccharides obtained from the cell walls of gram-negative bacteria.

7. The method of claim 6, for use in treating ovarian tumors, wherein the liposomes are administered by intraperitoneal injection, in a therapeutically effective amount.

8. A liposome composition for treating cancerous tumors in a mammal in need of such treatment comprising liposomes containing adriamycin and an immunostimulator effective to enhance the induction of host defenses in lymphoid cells by adriamycin.

9. The composition of claim 8, wherein the composition is an aqueous suspension containing adriamycin and macrophage stimulator predominantly in liposome-entrapped form.

10. The composition of claim 8, wherein the macrophage stimulator is selected from the group consisting of lipopolysaccharides obtained from the cell walls of gram-negative bacteria.

11. The composition of claim 10, wherein the liposomes also contain a secondary compound which acts to reduce the toxicity of adriamycin, and is selected from the group consisting of N-acetylcysteine, niacin, isocitrate, hydroxybutylated toluene, and alpha-tocopherol, and analogues thereof, including alpha-tocopherol succinate.

12. A method of enhancing the tumoricidal activity of macrophages, as evidenced by the ability of isolated macrophages to lyse mastocytoma cells in culture, comprising administering in vivo a suspension of liposomes with entrapped adriamycin, and exposing the macrophages from the subject receiving the suspension to an immunostimulator.

13. The method of claim 12, wherein the immunostimulator is a lipopolysaccharide obtained from the cell walls of gram-negative bacteria.

14. The method of claim 12, wherein the microphages are exposed to the stimulator in vitro and which further includes introducing the stimulated macrophages in vivo.

15. The method of claim 12, wherein the adriamycin-containing liposomes are administered by intraperitoneal injection, in a liposome suspension containing a pharmacologically effective amount of adriamycin.

16. The method of claim 15, for use in treating ovarian cancer, wherein said exposing includes administering a pharmaceutically effective amount of macrophage stimulator within a period up to about 18 days after said administering.

17. The method of claim 16, wherein the adriamycin and immunostimulator are coentrapped in the same liposomes.

* * * * *